US011699425B2

(12) United States Patent
Ozluturk

(10) Patent No.: US 11,699,425 B2
(45) Date of Patent: *Jul. 11, 2023

(54) METHOD AND APPARATUS FOR NOISE CANCELLATION IN A WIRELESS MOBILE DEVICE USING AN EXTERNAL HEADSET

(71) Applicant: Fatih Mehmet Ozluturk, Sands Point, NY (US)

(72) Inventor: Fatih Mehmet Ozluturk, Sands Point, NY (US)

( * ) Notice: Subject to any disclaimer, the term of this patent is extended or adjusted under 35 U.S.C. 154(b) by 320 days.

This patent is subject to a terminal disclaimer.

(21) Appl. No.: 16/670,554

(22) Filed: Oct. 31, 2019

(65) Prior Publication Data

US 2020/0068289 A1 Feb. 27, 2020

Related U.S. Application Data

(63) Continuation of application No. 15/972,379, filed on May 7, 2018, now Pat. No. 10,469,936, which is a (Continued)

(51) Int. Cl.

| *G10K 11/178* | (2006.01) |
| *G10K 11/175* | (2006.01) |
| *G06F 3/16* | (2006.01) |
| *G10L 21/0208* | (2013.01) |
| *H04R 1/10* | (2006.01) |

(Continued)

(52) U.S. Cl.
CPC ........ *G10K 11/17823* (2018.01); *G06F 3/165* (2013.01); *G10K 11/175* (2013.01); *G10K 11/17821* (2018.01); *G10K 11/17827* (2018.01); *G10K 11/17855* (2018.01); *G10K 11/17857* (2018.01); *G10K 11/17873* (2018.01); *G10K 11/17885* (2018.01); *G10L 21/0208* (2013.01); *H04B 3/23* (2013.01); *H04R 1/1083* (2013.01); *A61F 11/145* (2022.01); *G10K 2210/1081* (2013.01)

(58) Field of Classification Search
USPC ................................................. 381/71.1, 71.6
See application file for complete search history.

(56) References Cited

U.S. PATENT DOCUMENTS

| 7,567,677 B1 | 7/2009 | Chan et al. |
| 7,706,821 B2 | 4/2010 | Konchitsky |

(Continued)

*Primary Examiner* — Disler Paul
(74) *Attorney, Agent, or Firm* — Volpe Koenig

(57) ABSTRACT

A method, system, and apparatus for noise cancelation is disclosed, which may be used in a wireless unit (WU). The WU may include a processor, a memory, a user interface, internal microphones and internal speakers. A removably connected headset may include microphones and speakers. The WU may receive a first ambient noise from headset microphone(s), which may generate a first signal based on the first ambient noise. The WU may receive a second ambient noise at internal microphone(s), which may generate a second signal based on the second ambient noise. The WU may calculate an estimate of ambient noise based on the first and second signals, calculate a signal for noise cancellation based on the estimate, cancel estimated ambient noise from an audio output signal based on an application of the signal for noise cancellation, and send the audio output signal to speakers of the headset or of the WU.

10 Claims, 8 Drawing Sheets

Related U.S. Application Data continuation of application No. 15/477,623, filed on Apr. 3, 2017, now Pat. No. 9,967,651, which is a continuation of application No. 14/629,096, filed on Feb. 23, 2015, now Pat. No. 9,613,611.

(60) Provisional application No. 61/943,521, filed on Feb. 24, 2014.

(51) Int. Cl.
*H04B 3/23* (2006.01)
*A61F 11/14* (2006.01)

(56) References Cited

U.S. PATENT DOCUMENTS

| | | | |
|---|---|---|---|
| 7,761,106 B2 | 7/2010 | Konchitsky | |
| 8,379,871 B2 | 2/2013 | Michael et al. | |
| 8,447,045 B1* | 5/2013 | Laroche | G10K 11/17825 |
| | | | 381/71.8 |
| 9,344,792 B2 | 5/2016 | Rundle | |
| 9,414,964 B2 | 8/2016 | Censo et al. | |
| 9,716,939 B2 | 7/2017 | Di Censo et al. | |
| 2001/0050993 A1* | 12/2001 | Douglas | G10K 11/17857 |
| | | | 381/71.6 |
| 2007/0274552 A1 | 11/2007 | Konchitsky et al. | |
| 2010/0131269 A1 | 5/2010 | Park et al. | |
| 2011/0116643 A1 | 5/2011 | Tiscareno et al. | |
| 2012/0250873 A1 | 10/2012 | Bakalos et al. | |
| 2013/0108068 A1* | 5/2013 | Poulsen | H04R 5/033 |
| | | | 381/74 |
| 2013/0216050 A1 | 8/2013 | Chen et al. | |
| 2014/0044275 A1* | 2/2014 | Goldstein | H04R 1/1083 |
| | | | 381/71.6 |
| 2014/0355775 A1* | 12/2014 | Appelbaum | H04R 29/005 |
| | | | 381/71.1 |
| 2015/0003622 A1 | 1/2015 | Lee et al. | |
| 2015/0055789 A1 | 2/2015 | Castilo et al. | |
| 2015/0161981 A1 | 6/2015 | Kwatra | |

* cited by examiner

METHOD AND APPARATUS FOR NOISE CANCELLATION IN A WIRELESS MOBILE DEVICE USING AN EXTERNAL HEADSET

CROSS REFERENCE TO RELATED APPLICATIONS

This application is a continuation of U.S. patent application Ser. No. 15/972,379 filed May 7, 2018, which is a continuation of U.S. patent application Ser. No. 15/477,623 filed Apr. 3, 2017, which issued as U.S. Pat. No. 9,967,651 on May 8, 2018, which is a continuation of U.S. patent application Ser. No. 14/629,096 filed Feb. 23, 2015, which issued as U.S. Pat. No. 9,613,611 on Apr. 4, 2017, which claims the benefit of U.S. Provisional Application No. 61/943,521 filed Feb. 24, 2014, the contents of which are hereby incorporated by reference herein.

FIELD OF INVENTION

The disclosed embodiments are generally directed to a method and apparatus in the field of wireless mobile devices. More specifically, the disclosed embodiments are directed to reducing or canceling ambient noise when a wireless mobile device headset is used.

BACKGROUND

When a user is listening to an audio output from a wireless device, such as a phone conversation, music or an audio component of a multimedia content, the user may also hear ambient noise. Ambient noise may be produced by people, equipment, traffic, or even other multimedia devices nearby, and is undesirable. The goal of noise cancelation is to somehow reduce or remove the ambient noise so that the user hears only the desired audio output from the wireless device.

Current noise cancelation techniques may include a set of speakers and a set of microphones in each ear cup of a noise canceling headset. The microphones are typically positioned in proximity to the outside of the ear cups to detect the ambient noise, whereas the speaker may also be positioned on the inside of the ear cup to subtract the ambient noise from the intended audio that is also played into the ear on the inside of the ear cups. To do the processing, headphones may include a processor to receive the input from the ambient noise detecting microphones on the outside of the ear cup, then calculate the noise estimate, and then play back the inverted (or negative) version of the ambient noise from the speakers on the inside of the ear cup. The processor may also scale the noise estimate because there is inherent isolation from the outside of the ear cups to the inside, which reduces the level of ambient noise on the inside of the ear cups. Since this process takes some processing power from an electronic computation device, the noise canceling headphones may require batteries as well.

SUMMARY

A method, system, and apparatus for noise cancelation is disclosed herein, which may be used in a wireless unit (WU) and a headset removably connected to the WU. In an example, the WU may include a processor, a memory, a user interface, internal microphones and internal speakers. The headset may include microphones and speakers, and be powered by the WU. The WU may receive a first ambient noise from one or more microphones of the headset, and receive a second ambient noise at one or more internal microphones. The one or more microphones of the headset may generate a first signal based on the first ambient noise. The one or more internal microphones may generate a second signal based on the second ambient noise. The WU processor may then calculate an estimate of ambient noise based on the first signal and the second signal. The processor of the WU may then calculate a signal for noise cancellation based on the estimate of ambient noise, cancel estimated ambient noise from an audio output signal based on an application of the signal for noise cancellation, and send the audio output signal to the speakers of the headset or the internal speakers of the WU.

In a further example, the WU may include a processor, a memory, a user interface, internal microphones and internal speakers. The headset may include microphones and speakers, and be powered by the WU. The WU may receive a first ambient noise from one or more microphones of the headset. The one or more microphones of the headset may then generate a first signal based on the first ambient noise and the processor of the WU may calculate an estimate of ambient noise based on the first signal. The processor of the WU may then calculate a signal for noise cancellation based on the estimate of ambient noise, cancel estimated ambient noise from an audio output signal based on an application of the signal for noise cancellation, and send the audio output signal to the speakers of the headset or the internal speakers of the WU.

In another example, the WU may receive a second ambient noise at one or more internal microphones. The one or more internal microphones may then generate a second signal based on the second ambient noise. The WU processor may then calculate an estimate of ambient noise based on the first signal, the second signal and an operating parameter.

Through the use of a standard headset with one or more microphones and one or more speakers, the noise cancelation technique described herein may use the processing power of the mobile phone, and may require no other additional hardware. Further, the noise cancelation described herein can be implemented as a standalone software application, as part of another software application, or as part of the operating system or middleware of the WU.

Further, the noise cancelation may include receiving and applying input from a user. The user input may indicate one or more operating parameters. Further, the user input may indicate one or more phase shifts. Also, the user input may include selecting one or more of the internal microphones, or selecting one or more of the headset microphones, or selecting both. In addition, the user input may include selecting one or more ambient noise components for canceling. Moreover, the noise cancelation may include calculating a Fast Fourier Transform (FFT) of the signal.

Further, the noise cancelation may include receiving and applying input from a user. The user input may indicate one or more scaling factors. Further, the user input may indicate one or more phase shifts. Also, the user input may include selecting one or more of the internal microphones, or selecting one or more of the headset microphones, or selecting both. In addition, the user input may include selecting one or more ambient noise components for canceling. Moreover, the noise cancelation may include calculating a Fast Fourier Transform (FFT) of the signal.

In an additional example, the headset may be powered by the WU via a connector. In another example, the headset may be without a processor.

DETAILED DESCRIPTION

The method and apparatus disclosed herein may apply to mobile wireless devices, including, for example but not limited to, cell phones, feature phones, smart phones, tablet PCs with wireless connectivity, and all future devices that generally share similar characteristics. As used herein, a microphone may refer to a single microphone or one or more microphones and the terms may be used interchangeably. As used herein, a speaker may refer to a single speaker or one or more speakers and the terms may be used interchangeably. As used herein, a wireless unit (WU) may refer to a mobile device that is able to wirelessly transmit or receive digital or analog data or voice information, a wireless device or a mobile wireless device, and the terms may be used interchangeably.

Figure 1:
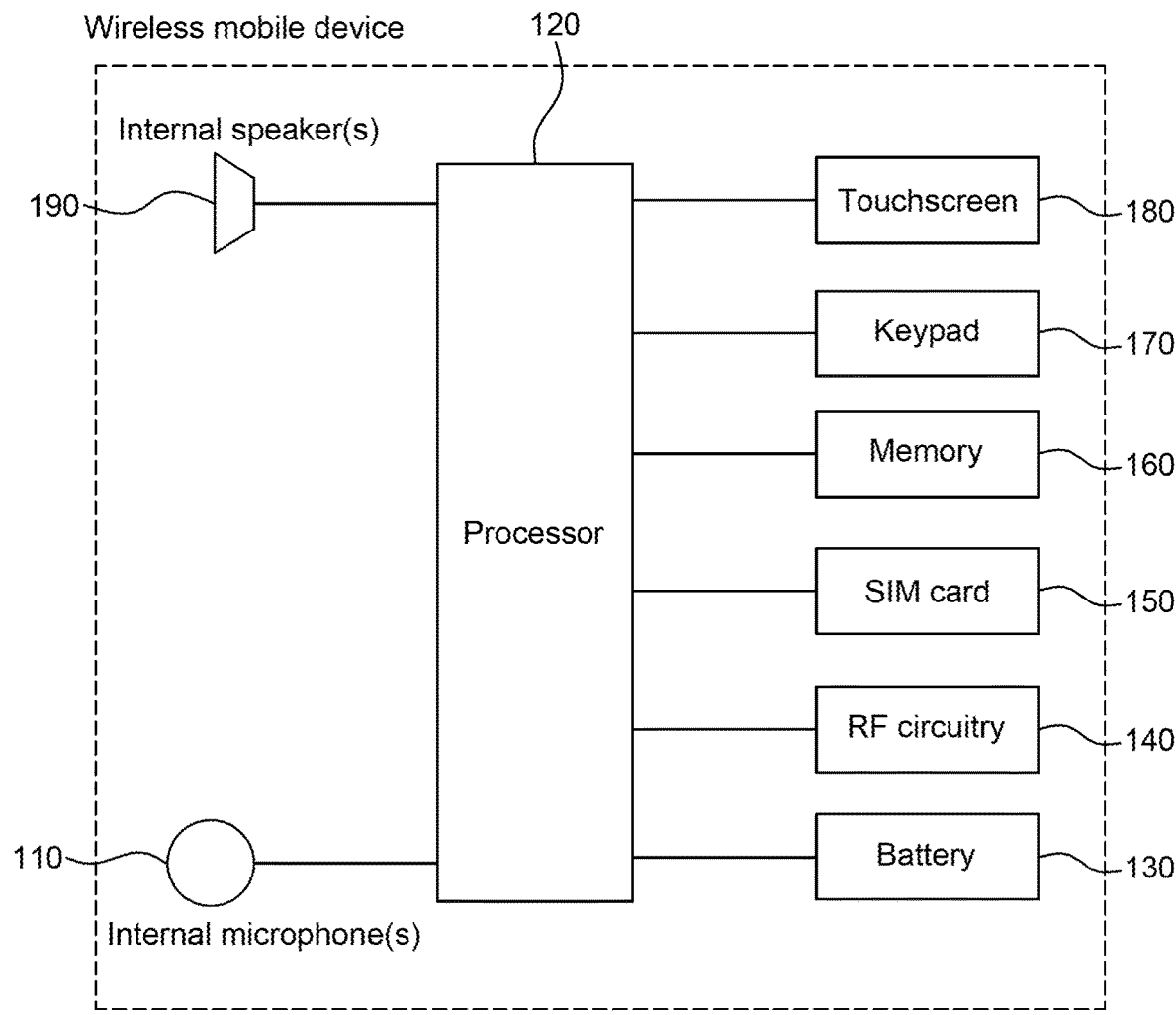
FIG. 1 is a system diagram of an example wireless unit (WU) that may use one or more embodiments disclosed herein.

FIG. 1 is a system diagram of an example wireless unit (WU) that may use one or more embodiments disclosed herein. As may be typical for wireless mobile devices, the WU in FIG. 1 includes a processor 120 that may manage several peripherals and components. As may also be typical for wireless mobile devices, the WU may include components such as a battery 130 as a power supply, memory 160 to execute programs, a subscriber identity module (SIM) such as a SIM card 150, and user input/output devices such as a keypad 170 or a touchscreen 180 or both. The WU may also include RF circuitry 140, as shown in FIG. 1, and an antenna (not shown) to facilitate the wireless connectivity. As one of ordinary skill in the art will understand, the WU may also use more than one processor and, if so, the processors may perform different tasks. Moreover, there may be additional storage, removable storage components, as well as other peripherals such as one or more cameras, a flash memory, circuitry for the user of a global positioning system (GPS) applications, BLUETOOTH, infrared, near-field communications (NFC) components, and others. The figures and description herein may use a simplified representation of the WU as the methods described herein may use a variety of WU components. In an example, a WU may not include one or more of the components that we described above.

The WU may also use one or more internal speakers 190, one or more internal microphones 110, and a connector plug (not shown) for electrical connection to an external headset. Internal speakers 190 and microphones 110 may be used for making voice and multimedia calls. In other words, the user may speak or input other audio input through the microphones 110 and may hear voice or other audio output from the speakers 190. The headset, when plugged into the connector, may serve the same purpose. One or more microphones on the headset may be used for inputting audio, and one or more speakers on the headset may be used for outputting of audio by the mobile device.

Figure 2:
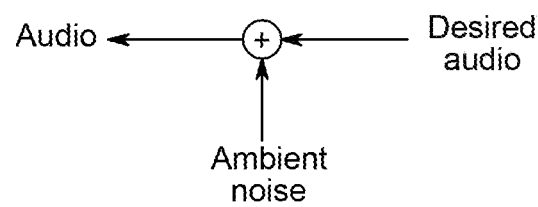
FIG. 2 is a diagram of an example of a basic representation of audio that a user may hear.

FIG. 2 is a diagram of an example of a representation of the audio information that a user may hear. In an example, a basic representation of the audio that the user may hear may be:

$$\text{audio} = \text{desired audio from the device} + \text{ambient noise} \quad \text{Equation (1)}$$

In Equation (1), audio may be what the user actually hears, and ambient noise may be the undesirable component, as shown in FIG. 2. This may be the case, for example when the user is listening to an audio output from the wireless device, such as a phone conversation, music, or audio component of a multimedia content. Ambient noise may be produced by people, equipment, traffic, or even other multimedia devices nearby, and is typically undesirable. In this scenario, the goal of noise cancelation may be to somehow remove the ambient noise so that the user may hear:

$$\text{audio} = \text{desired audio from the device} \quad \text{Equation (2)}$$

Figure 3:
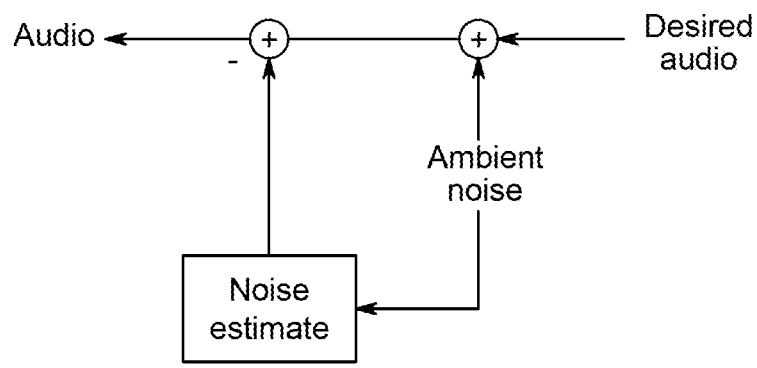
FIG. 3 is a diagram of an example of a representation of noise cancelation.

FIG. 3 is a diagram of an example of a representation of noise cancelation. In another example, at a basic level, noise cancelation may work by estimating the ambient noise and subtracting it from the audio presented to the user, as shown in FIG. 3. In other words:

$$\text{audio} = \text{desired audio from the device} - \text{estimate of ambient noise} + \text{ambient noise} \quad \text{Equation (3)}$$

$$\text{audio} = \text{desired audio from the device} + \text{residual noise} \quad \text{Equation (4)}$$

In equation (4), the residual noise may be small, ideally zero, if the ambient noise is estimated perfectly.

Figure 4:
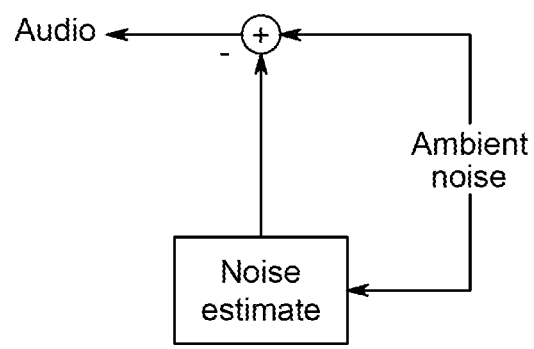
FIG. 4 is a diagram of another example of a representation of noise cancelation.

FIG. 4 is a diagram of another example of a representation of noise cancelation. In another scenario, noise cancelation may be used in absence of any desired audio from the mobile device, as shown in FIG. 4. In other words:

$$\text{audio} = \text{ambient noise} \quad \text{Equation (5)}$$

In Equation (5), ambient noise may be corrected by noise cancelation. This may produce:

$$\text{audio} = \text{ambient noise} - \text{estimate of ambient noise} \quad \text{Equation (6)}$$

$$\text{audio} = \text{residual noise} \quad \text{Equation (7)}$$

In Equation (7), the residual noise may ideally be zero, that is, silence.

Additional microphones and speakers as well as the processor and battery make current noise canceling headphones too heavy, too bulky, and much too expensive. In addition, since these headphones require batteries of their own to operate, the user has to either replace the batteries from time to time or charge them, which makes them inconvenient. Examples disclosed herein describe noise cancelation technology that may be easy to use, cheap, light, and may not require its own battery.

A method, system, and apparatus are disclosed herein for implementing noise cancelation using the existing components of a wireless mobile device, and a headset with a speaker and microphone. The technique described may make use of the processor and power source within the mobile device and hence may not require its own battery. Examples disclosed herein make use of the internal speaker and microphone included in the wireless mobile device, and the speaker and microphone of a headset that may be plugged into the mobile device.

Figure 5:
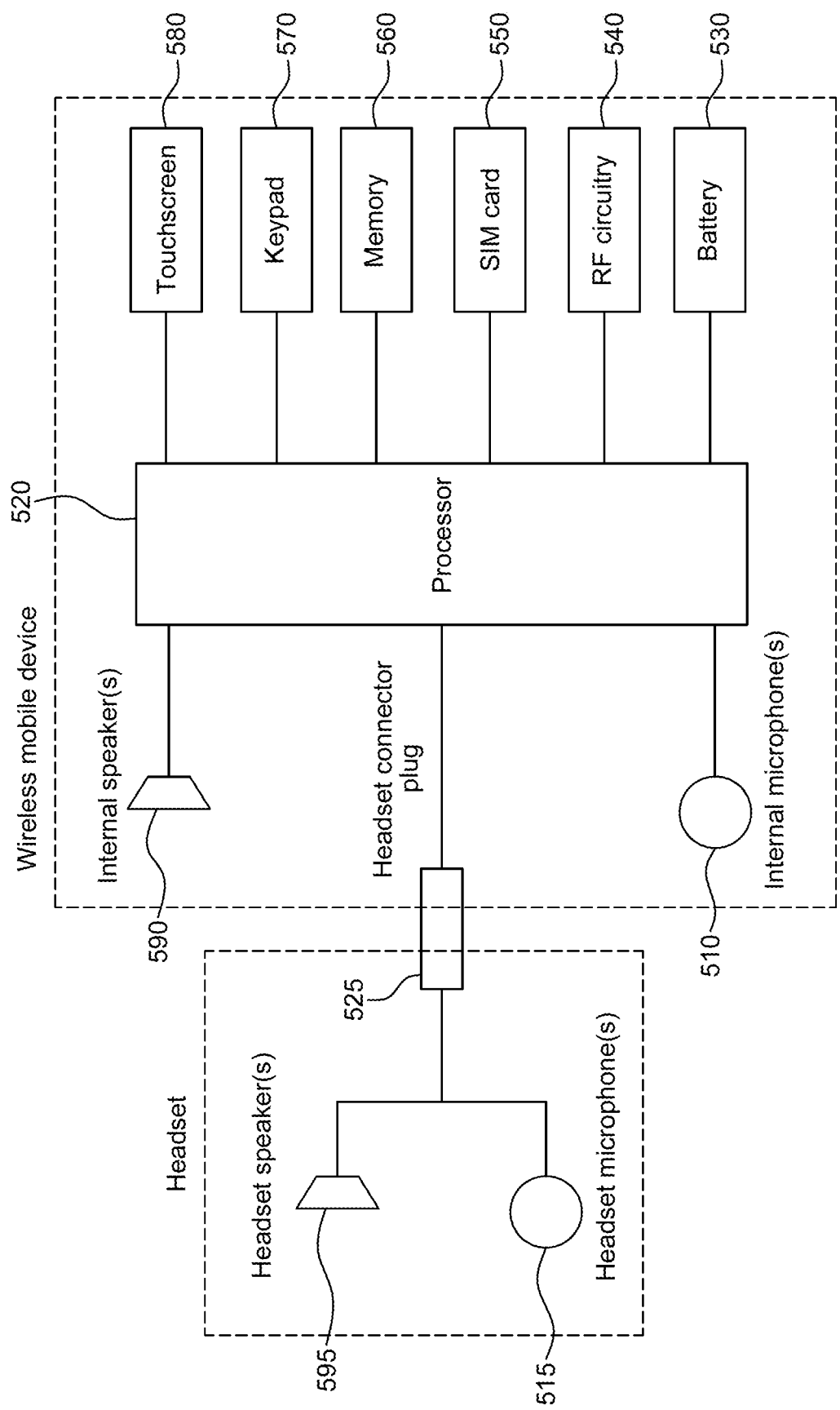
FIG. 5 is a system diagram of an example WU and headset that may use one or more embodiments disclosed herein.

FIG. 5 is a system diagram of an example WU and headset that may use one or more embodiments disclosed herein. The microphone 510 on the WU and the microphone 515 on the headset may be used selectively to detect the ambient noise.

The ambient noise is selectively detected by the microphone 510 on the headset, the microphone 515 on the WU, or both, and may then be processed by the processor 520 in the WU to create the noise estimate. The headset microphone 510, WU microphone 515, or both, may generate a signal based on the ambient noise and send the signal to the processor to create the noise estimate. The processor 520 may then subtract the estimated ambient noise from the audio that may be delivered to the WU internal speaker(s) 590, the headset speakers 595, or both, thereby canceling the effect of the ambient noise. The WU may also include components such as a battery 530 as a power supply, memory 560 to execute programs, a SIM card 550, and user input/output devices such as a keypad 570 or a touchscreen 580 or both. The WU may also include RF circuitry 540 and an antenna (not shown) to facilitate the wireless connectivity. The headset may be removably connected to the wireless mobile device with a headset connector plug 525. The WU may provide power to the headset. As a result, the headset may not include a battery or other power source. In a further example, the headset may also not include a processor.

In a further example, the headset may include speakers(s) but not a microphone, and only the microphone of the mobile device detects the ambient noise. The mobile device microphone may then generate a signal based on the ambient noise and send the signal to the processor to create the noise estimate. The processor may then subtract the estimated ambient noise from the audio that may be delivered or sent to the WU internal speaker(s) 590, the headset speakers 595, or both, thereby canceling the effect of the ambient noise.

Software code, such as middleware, application software or as part of the operating system that runs on the processor 520 may perform the noise cancelation as described above. For simplicity, this software will be referred to herein as the noise cancelation application (NCA). One of ordinary skill in the art will understand that the software may be embedded code, middleware, an application, part of the operating system, and the like. A variety of classifications of the software may be used with the examples described herein.

Besides controlling the processor to do the main elements of the noise cancelation, NCA may also include a user interface where the user may provide input and also see performance and diagnostic data from the noise cancelation process. One of the inputs from the user may be a scale factor which determines how the noise estimate is scaled before subtraction. Another input may be to select whether the headset speakers, mobile device speakers, or both are used in detecting the ambient noise.

The examples disclosed herein may require no additional hardware beyond the wireless mobile device itself and a headset with speaker(s) only, or with speakers and one or more microphones. Such headsets are widely available and cost very little, especially compared to the current noise canceling headphones on the market today. For comparison purposes, a simple headset that can be used to implement the examples disclosed herein may cost as little as $10-$20, whereas the noise canceling headphones from brands such as SONY, BOSE, and others may cost $250-$350 at current prices.

Figure 6:
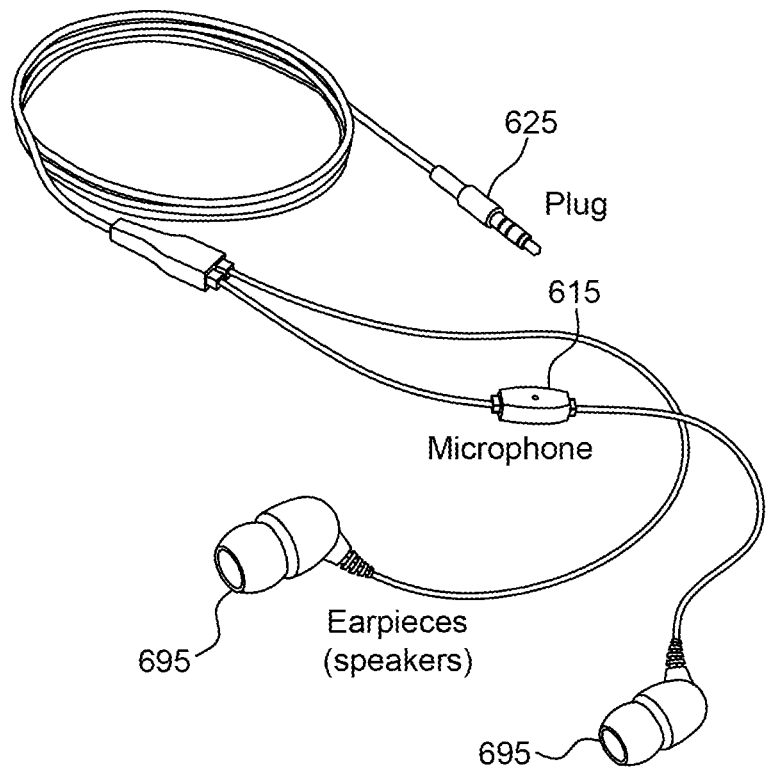
FIG. 6 is a diagram of an example of simple earphones that may use one or more embodiments disclosed herein.

FIG. 6 is a diagram of an example of simple earphones that may use one or more embodiments disclosed herein. In an example, the earphones or headset may include a connector or plug 625 to connect with the WU, a microphone 615 and earpieces or speakers 695. The earphones or headset may removably connect to the WU with the connector or plug 625.

In a further example, the earphones or headset may include a plug to connect with the WU, earpieces or speakers, but no microphone. In yet a further example, the earphones or headset may include a plug to connect with the WU and a microphone but no earpieces or speakers.

Figure 7:
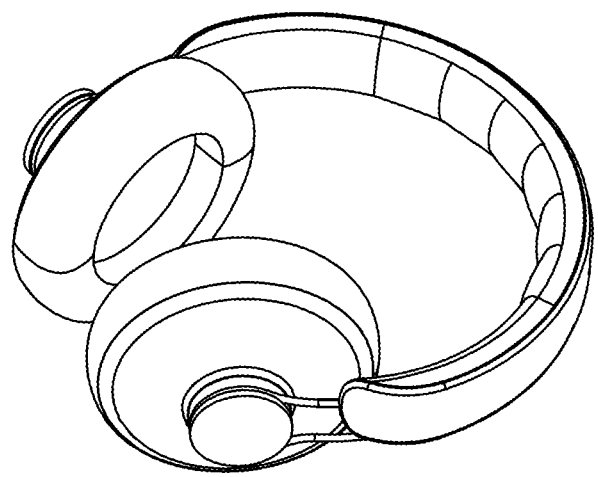
FIG. 7 is a diagram of an example of noise canceling headphones.

FIG. 7 is a diagram of an example of noise canceling headphones. The noise canceling headphones may be used as standalone noise canceling headphones.

Figure 8:
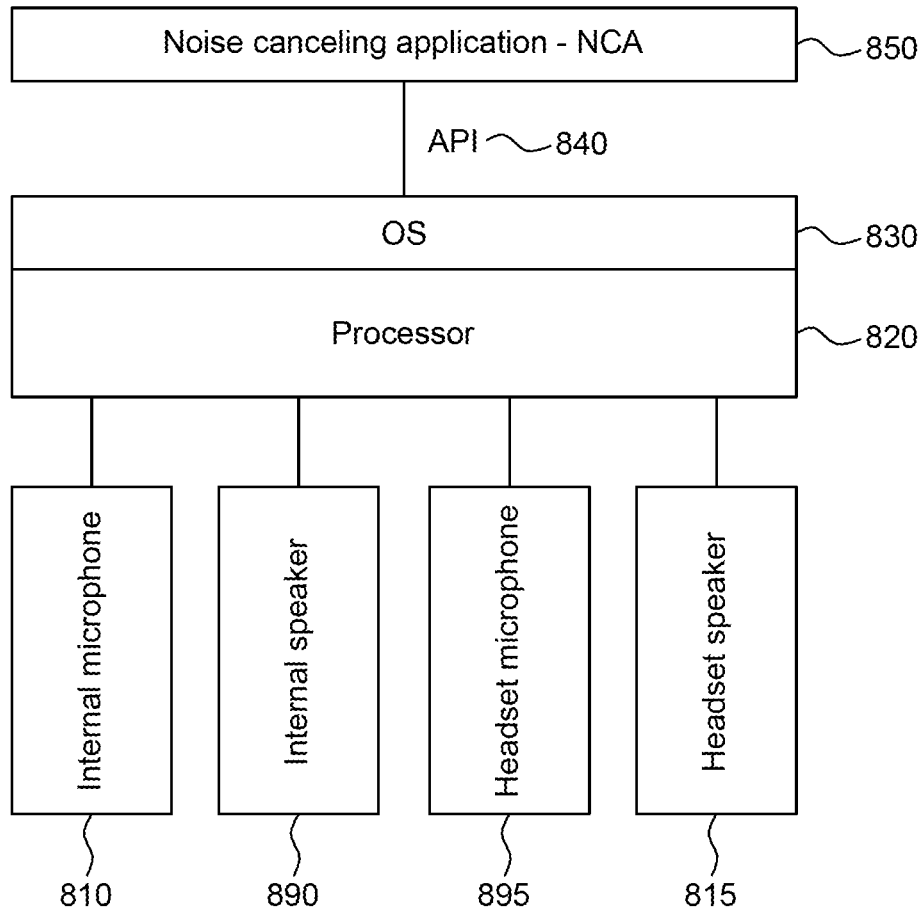
FIG. 8 is a diagram of an example of a noise cancelation application (NCA) in communication with an operating system (OS) and a processor.

FIG. 8 is a diagram of an example of an NCA 850 in communication with an operating system (OS) 830 and a processor 820. Wireless mobile devices such as a smartphone from APPLE (IPHONE) or a smartphone running on the ANDROID platform from SAMSUNG (GALAXY) make Application Programming Interfaces (APIs) available to developers. As shown in FIG. 8, the API 840 may describe the way one software application, such as the NCA 850, may communicate with another software application, such as the OS 830, and the processor 820 on which the OS 830 runs. The NCA 850 may use the standard APIs as API 840 to interface with the processor 820, and interact with the internal microphone 810, headset microphone 895, internal speaker 890 and headset speaker 815 as described.

Figure 9:
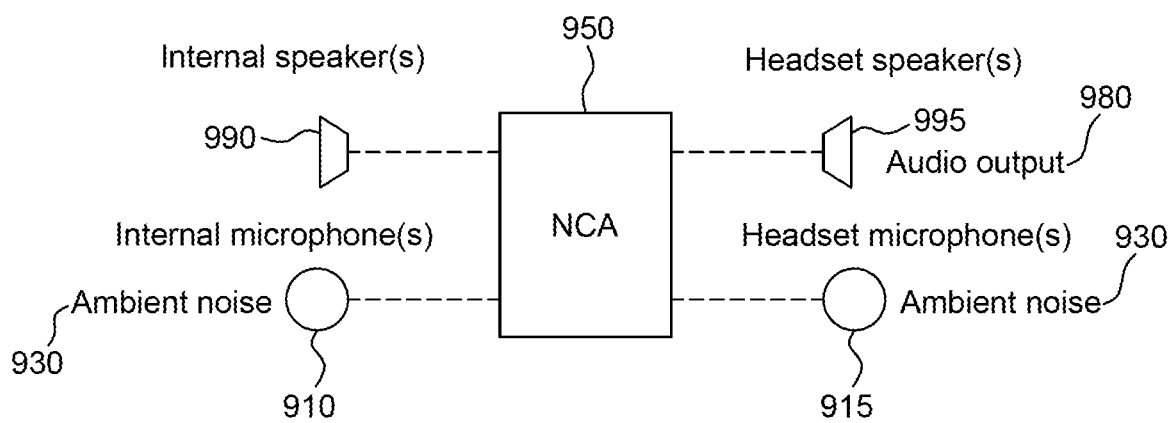
FIG. 9 is a diagram of an example of an NCA in communication with WU and headset microphones and speakers.

FIG. 9 is a diagram of an example of an NCA in communication with the WU and headset microphones and speakers. The NCA may have an indirect connection to the WU and headset components through the API, OS, and the processor, as shown by dotted lines in FIG. 8. The NCA may have an indirect connection to the internal mobile device microphone 910 and headset microphone 915. Both the microphone on the mobile device 910 and the microphone on the headset 915 may be receivers for receiving the ambient noise 930. The audio that may be detected by these microphones 910, 915 may be received by the NCA for further processing. Further, the NCA may have an indirect connection to the internal mobile device speaker 990 and headset speaker 995.

When the user is listening to audio portion of a multimedia content or is on a phone call, there may be a desired audio component. The ambient noise 930 may be subtracted from this audio component. In other words, the inverse of the ambient noise waveform may be added (or applied) to the audio component that is sent to the headset speaker 995. This can be written as:

$$s(t)=a(t)+n(t) \quad \text{Equation (8)}$$

In Equation (8), s(t) is the audio output signal 980 that the user hears when the user is wearing the headset and there is ambient noise. Further, a(t) is the desired audio signal such as the voice or media content coming from the headset earpiece of speaker 995, and n(t) is the ambient noise that the user hears. When the ambient noise is detected and an estimate of it is obtained, then the inverse of this noise estimate may be added (or applied) to the audio signal from the mobile device as follows:

$$s(t)=(a(t)-\hat{n}(t))+n(t) \quad \text{Equation (9)}$$

$$s(t)=a(t)+\varepsilon(t) \quad \text{Equation (10)}$$

In Equation (9) n̂(t) is the noise estimate. In Equation (10), ε(t) is the small residual noise after cancelation. When there is no desired audio component as above, then the user may be wearing the headset only for its noise canceling use. In that case, the inverse of the ambient noise waveform may be sent to the headset speaker 995. This canceling waveform may cancel the ambient noise that the user is hears. The cancelation can be shown as follows:

$$s(t)=(-\hat{n}(t))+n(t) \quad \text{Equation (11)}$$

$$s(t)=\varepsilon(t) \quad \text{Equation (12)}$$

In an example, two adjustments or calibrations may be used. These may improve performance of the noise canceler and can be used alone or in combination. Headsets, whether noise canceling or not, may have some level of noise isolation because they simply cover the ear opening and reduce the amount of sound waves penetrating. As a result, the ambient noise that goes through the earpiece of the headset and reaches the ear canal may be attenuated as compared to the ambient noise that is received by the mobile device microphone or the headset microphone. As a first example calibration, a calibration may be used to assure that the correct amount of noise is canceled. If this calibration is desired, the NCA may present the user with a calibration scale on the mobile device screen. The user may then change the calibration, in other words the noise scaling, and find the optimum level by listening to the headset at the same time. The calibration interface may be presented to the user as a slider, a dial, or any other virtual switch on the user interface. The user may set the desired setting on the touchscreen or may use any other button, such as the volume control switches to input the calibration level when the NCA prompts the user to do so. In an example, the calibration may be described mathematically as follows:

$$\hat{n}(t)=\alpha n_{headset}(t)+\beta n_{device}(t) \quad \text{Equation (13)}$$

In Equation 13, $n_{headset}(t)$ and $n_{device}(t)$ are the ambient noise that the headset microphone and mobile device microphone are detecting, respectively. As in equations above, n̂(t) is the estimate of the ambient noise that the user is hearing. Further, the noise detected by the headset microphone and the noise detected by the mobile device microphone may be scaled by α and β respectively. In example, these two scaling factors may be completely different, and set by the user separately, or they may be the same. Alternatively, they may be related to each other by another factor; one scaling factor may be some multiple of the other scaling factor. Further, either or both of the scaling factors may be set to zero.

A second calibration may be utilized to correct any small time shifts. Although the headset microphone or the mobile device microphone, or both, may be used to detect the ambient noise level, this may often not be exactly the same waveform that reaches the ear. This is because there may be a physical separation between the microphones and the ear, which may translate into a very small time shift (a phase shift) between the ambient noise the user hears and the ambient noise the microphones detects. Additionally, the processing in the processor is not instantaneous and may account for some time delay as well. If this phase shift is small, it may be imperceptible and may not affect noise cancelation performance. However if the phase shift is large, it may negatively affect the noise cancelation and may even make it worse than having no noise cancelation. This can be shown mathematically as follows:

$$\hat{n}(t)=\alpha n_{headset}(t-\tau_{headset})+\beta n_{device}(t-\tau_{device}) \quad \text{Equation (14)}$$

In Equation (14), the noise detected by the headset microphone and the noise detected by the device microphone are shifted (or delayed) by $\tau_{headset}$ and τdevice respectively, in addition to being scaled. Note that the two time shift values may be the same or different, or may be related to each other by an offset. Also note that either or both of the time shift values may be set to zero.

There are two example methods to correct the phase shift (time shift) if it is significant. One example method is to take the Fast Fourier Transform (FFT) of the ambient noise from the mobile device microphone and from the headset microphone, and calculate the shift amount that corresponds to the maximum correlation. The shift amount may be the time difference between the headset and mobile device microphones. If only one microphone, such as only the headset microphone, is used in detecting the ambient noise, then there may be no need for this step.

The second example method of correcting the time difference between the mobile device and headset microphones, and between the microphones and what the user hears through the headset speaker is to do this interactively. In this manner, the NCA may present the user with sliders, dials, or other visual ways to input these on the device screen. The user may find the optimum setting by changing the correction on the screen while listening to the headset.

Figure 10:
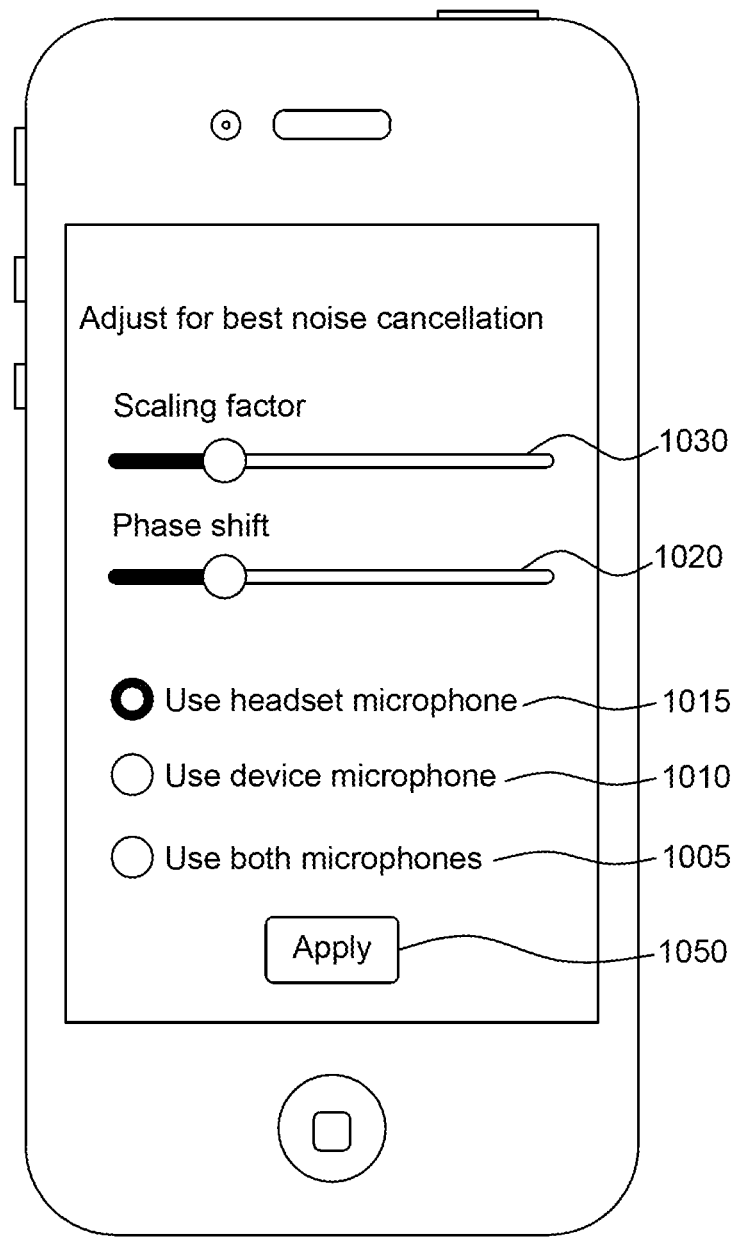
FIG. 10 is a diagram of an example user interface on a smartphone.

FIG. 10 is a diagram of an example user interface on a smartphone. In an example shown in FIG. 10, the user may select the calibration levels and adjust the parameters for best noise cancelation performance.

Figure 11:
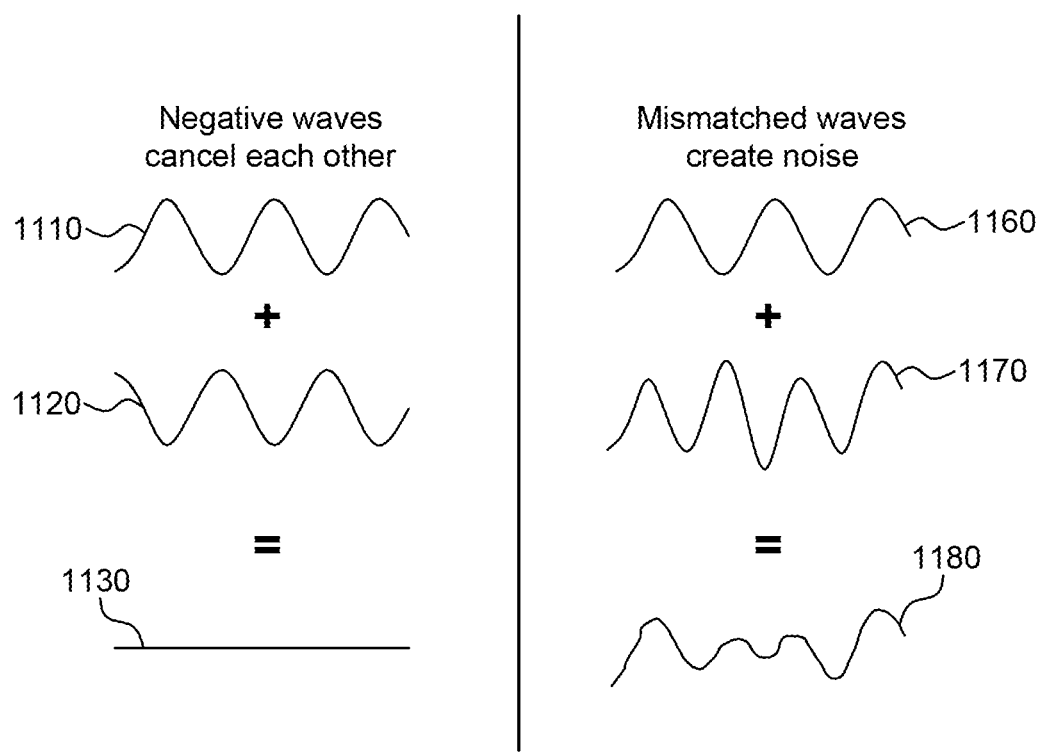
FIG. 11 is a diagram of an example waveform canceled by another wave.

FIG. 11 is a diagram of an example waveform canceled by another wave. An example cancelation process is shown in FIG. 11, which shows how a wave is canceled by another wave that is negative of it—in other words, an inverse of the original wave. For illustration purposes, the example in FIG. 11 shows only a sinusoidal wave, which corresponds to a single tone. Actual voice or other audio waveforms are typically more complex, and can be thought of as a combination of many sinusoidal waves. As FIG. 11 illustrates, the cancelation quality may depend on how well the original waveform 1110, 1160, in the example, the ambient noise, is estimated. If the estimate is close to the ambient noise being estimated 1120, there may be very little residual noise after the cancelation 1130. However if the estimate is poor 1170, the cancelation process may instead create additional noise 1180. Audio cancelation as described above may be the basis for many noise cancelation techniques. Further, in examples disclosed herein, the noise cancelation may use only the mobile device itself and a simple earphone type headset to perform the cancelation.

Various applications and use cases may use the technology disclosed herein. Below are some, but not necessarily all, example applications and use cases. The example applications and use cases are some, but not necessarily all, of the ways the technology disclosed herein may be used. As a result, these examples are not intended to be exhaustive. There are many other applications of the same principles and the same technology.

The first example use case may occur when a user wants to use the headset only for noise cancelation purposes and not listening to any other audio. In this case the user may wear the headset, plug the headset into the mobile device, start the NCA on the mobile device, and if necessary, adjust the scaling factor 1030 and time shift or phase shift 1020 using the controls presented by the NCA on the mobile device screen. The user may decide to use the headset microphone 1015, the mobile device microphone 1010 or both microphones 1005 for noise cancelation. When the user has completed the selections, the user may hit the "Apply" button 1050 and the NCA will apply the user's settings for noise cancelation. The effect is that the ambient noise the user hears will be canceled out and the user will experience much reduced noise or silence through the headset earpieces.

The second example use case is similar to the first example use case except that the user may be listening to an audio content, such as voice during a phone call or music from a media file, while still employing noise cancelation of the NCA. In this case the effect may be to reduce or eliminate the ambient noise and delivery of the clear audio content to the user through the headset. In this example use case, the user may start the NCA and make scaling 1030 and time shift 1020 adjustments if necessary, as in the first example use case.

In a third example use case, the NCA is not a standalone application but may be integrated into another media application that runs on the mobile device. Such media applications include those that may download or stream music from a content delivery network (CDN), such as PANDORA, SPOTIFY, AMAZON MP3 player, APPLE ITUNES, or similar. These media application may give the user access to the media content from a CDN either wirelessly—streaming real time—or from the storage on the mobile device itself. The NCA may be integrated into one of these media applications such that the features and user interface of the NCA may be included in the features and user interface of the media application. For example, the user can start a streaming music application such as PANDORA, and this application may present the user the option to start noise cancelation, option to adjust scaling 1030, and option to adjust time shift 1020. In an example, this may be considered as the "white-box" version of the NCA.

In a fourth example use case, the NCA may be included in the operating system (OS) or other resident middleware software on the mobile device itself. In this case, the features and controls of the NCA may be absorbed into the features and user interface of the OS or middleware, and may be accessible through the screens and menus of the OS or middleware. In effect, the NCA functionality may be resident on the mobile device and may work in conjunction with any media application, such as those mentioned in the third example use case, or by itself.

In the four example use cases described above, and in others that are not mentioned, the basic principle of estimating ambient noise through the headset microphone and/or through the mobile device microphone may be the same. The noise is received and estimated, a scaling factor may be applied, a time shift may be applied, and the resulting waveform may be inverted and added to the audio output signal sent to the user headset speakers.

There are alternative example implementations of the technology described above also. According to one such example variation, the noise cancelation application NCA may detect and selectively cancel individual frequency components or frequency bands. This may be the better option when there is an ambient noise source that is generating noise at a particular frequency or a frequency band. It may be easier to detect that frequency component, invert it, and cancel it from the audio delivered to the user.

When working in this example alternative implementation, the NCA may calculate the FFT of the detected ambient noise and select a number of frequency components as candidates for cancelation. Then the scaling and time shift may be performed with or without user input as before, and the inverse of those noise components may be added to the audio component sent to the user's headset—thereby canceling the offending noise components that the user is hearing from the ambience.

Another alternative implementation may include calculating the frequency composition of the ambient noise, for example by using an FFT, and calculating the frequency composition of any desirably audio signal, for example by using an FFT, and deciding which frequency components of the ambient noise are likely to interfere with the desirable audio signal, and subtracting those frequency components from the audio sent to the microphones. A feature of this example may include presenting to the user a representation of the frequency components of the ambient noise, for example in the form of a bar chart on the touchscreen, and receiving input from the user indicating which frequency components to subtract. Alternatively the frequency components that are likely to interfere with the desired audio signal may be automatically subtracted without requiring user input. In the case that there is no desirable audio and the user is using the headset only to cancel out the ambient noise so the user can achieve silence, then all of the frequency components of the ambient noise may be undesirable. In this case a signal to subtract all of frequency components of the ambient noise may be generated and used to cancel the effect of the ambient noise. In another example, the highest, in other words most interfering, frequency components of the ambient noise may be selected and noise cancellation may be applied only to those components as well. In an example where the user is presented with a representation of the frequency components of the ambient noise, the user may be able to select in the user interface the components to be subtracted, and further select the scaling factor and phase shift to be applied.

In an example, the user interface for receiving user input for the scaling factor and for the phase shift do not need to label these inputs as scaling factor or phase shift, but rather they may be labeled in a way that may make it easier for the user to understand and use the user interface.

In a further example, the headset may connect to the WU wirelessly, instead of using or in addition to the connector plug. The headset may connect to the WU wirelessly using, for example, the BLUETOOTH standard.

Other alternative implementations are possible without being outside the principles and methods described herein. The implementations and variations of those described herein are not meant to be limiting of the scope of the technology to those implementations, but they are simply examples to show the general working principles. One of ordinary skill in the art will understand that the variations and different use cases described here can be used in combination.

Although features and elements are described above in particular combinations, one of ordinary skill in the art will appreciate that each feature or element may be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as compact disk (CD)-ROM disks, and digital versatile disks (DVDs). A processor in association with software may be used to implement a radio frequency transceiver for use in a WU, user equipment (UE), terminal, base station, a radio network controller (RNC), or any host computer.

What is claimed is:

1. A method of performing noise cancellation in a system, wherein the system includes a wireless unit (WU), wherein the WU includes a processor, a memory, a user interface, a connector, one or more internal microphones, and one or more internal speakers, and a headset removably connected to the WU and powered by the WU via the connector, the method comprising:
receiving, at one or more microphones of the headset, a first ambient noise, wherein the headset is without a processor and includes one or more speakers;
receiving, at the one or more internal microphones, a second ambient noise;
generating, by the one or more microphones of the headset, a first signal based on the first ambient noise;
generating, by the one or more internal microphones, a second signal based on the second ambient noise;
receiving, by the WU via the connector, the first signal;
calculating, by the processor of the WU, an estimate of ambient noise based on the first signal and the second signal;
further calculating, by the processor of the WU, a signal for noise cancellation based on the estimate of ambient noise, wherein the processor of the WU determines one or more phase shifts, and wherein the calculating the signal for noise cancellation is further based on the one or more phase shifts;
canceling, by the processor of the WU, estimated ambient noise from an audio output signal based on an application of the signal for noise cancellation; and
sending, by the processor of the WU, the audio output signal to the one or more speakers of the headset or the one or more internal speakers of the WU.

2. The method of claim 1, wherein the canceling of the estimated ambient noise is performed by a noise cancelling application (NCA) executed in the memory and the processor of the WU.

3. The method of claim 2, wherein the NCA is a software application, a middleware, a part of another media software application, or a part of an operating system of the WU.

4. The method of claim 1, wherein the processor of the WU selects one or more ambient noise components for canceling.

5. The method of claim 1, wherein the canceling of the estimated ambient noise includes calculating a Fast Fourier Transform (FFT) of the first signal.

6. A system for use in performing noise cancellation, the system comprising:
a headset without a processor comprising:
one or more microphones configured to receive a first ambient noise and to generate a first signal based on the first ambient noise; and
one or more speakers;
wherein the headset is powered by a wireless unit (WU) via a connector of the WU removably connected to the headset; and
the WU comprising:
a user interface;
a memory;
a processor operatively coupled to one or more internal microphones, to the memory and to the user interface, the processor configured to receive the first signal;
the connector operatively coupled to the processor;
one or more internal speakers of the WU configured to receive a second ambient noise and to generate a second signal based on the second ambient noise; and
the processor configured to calculate an estimate of ambient noise based on the first signal and the second signal, calculate a signal for noise cancellation based on the estimate of ambient noise, determine one or more phase shifts, cancel estimated ambient noise from an audio output signal based on an application of the signal for noise cancellation, and send the audio output signal to the one or more speakers of the headset or the one or more internal speakers of the WU, wherein the calculating of the signal for noise cancellation is further based on the one or more phase shifts.

7. The system of claim 6, wherein a noise cancellation application (NCA) in the WU performs the canceling of the estimated ambient noise and is executed in the memory and the processor of the WU.

8. The system of claim 7, wherein the NCA in the WU is a software application, a middleware, a part of another media software application, or a part of an operating system of the WU.

9. The system of claim 6, wherein the processor is further configured to select one or more ambient noise components for canceling.

10. The system of claim 6, wherein the canceling of the estimated ambient noise includes calculating a Fast Fourier Transform (FFT) of the first signal.

* * * * *